United States Patent
Tingvatn

(10) Patent No.: US 12,402,787 B2
(45) Date of Patent: Sep. 2, 2025

(54) MEDICAL VISUAL EXAMINATION AND SAMPLING DEVICE

(71) Applicant: ArtiMed AS, Bergen (NO)

(72) Inventor: Arly Tingvatn, Bergen (NO)

(73) Assignee: ArtiMed AS, Bergen (NO)

( * ) Notice: Subject to any disclaimer, the term of this patent is extended or adjusted under 35 U.S.C. 154(b) by 596 days.

(21) Appl. No.: 17/415,208

(22) PCT Filed: Dec. 17, 2019

(86) PCT No.: PCT/EP2019/085643
§ 371 (c)(1),
(2) Date: Jun. 17, 2021

(87) PCT Pub. No.: WO2020/127260
PCT Pub. Date: Jun. 25, 2020

(65) Prior Publication Data
US 2022/0061650 A1 Mar. 3, 2022

(30) Foreign Application Priority Data
Dec. 18, 2018 (GB) ..................... 1820602

(51) Int. Cl.
*A61B 1/303* (2006.01)
*A61B 1/00* (2006.01)
(Continued)

(52) U.S. Cl.
CPC .......... *A61B 1/303* (2013.01); *A61B 1/00016* (2013.01); *A61B 1/0008* (2013.01);
(Continued)

(58) Field of Classification Search
CPC ......... A61B 1/303; A61B 1/31; A61B 1/0008; A61B 1/32
See application file for complete search history.

(56) References Cited

U.S. PATENT DOCUMENTS 2,769,441 A * 11/1956 Abramson ............... A61B 1/31
600/184
3,417,746 A 12/1968 Moore et al.
(Continued)

FOREIGN PATENT DOCUMENTS

CN 104382551 A 3/2015
DE 202005019780 U1 4/2006
(Continued)

OTHER PUBLICATIONS

Final Office Action for U.S. Appl. No. 16/626,803, mailed Oct. 8, 2021, 10 pages.
(Continued)

*Primary Examiner* — Eduardo C Robert
*Assistant Examiner* — Holly Joanna Lane
(74) *Attorney, Agent, or Firm* — Withrow + Terranova, PLLC; Vincent K. Gustafson

(57) ABSTRACT

A device suitable for direct visual examination and sample collection from the digestive tract and vagina. The device comprises a main body and an observation channel situated inside the main body comprising a first closed end and a second end. The device further comprises an obturator for insertion into the main body, the obturator comprising a longitudinal groove arranged to accommodate the observation channel and a tip comprising a resiliently deformable portion. The resiliently deformable portion is adapted to deform to allow the obturator to pass over the observation channel as the obturator is being inserted into the main body and to restore to its original shape once the tip has passed over the observation channel and the obturator is fully inserted into the main body.

20 Claims, 7 Drawing Sheets

(51) Int. Cl.
*A61B 1/015* (2006.01)
*A61B 1/04* (2006.01)
*A61B 1/31* (2006.01)
*A61B 1/32* (2006.01)
*A61B 10/04* (2006.01)

(52) U.S. Cl.
CPC .......... *A61B 1/00103* (2013.01); *A61B 1/015* (2013.01); *A61B 1/04* (2013.01); *A61B 1/32* (2013.01); *A61B 10/04* (2013.01); *A61B 1/00066* (2013.01); *A61B 1/31* (2013.01)

(56) References Cited

U.S. PATENT DOCUMENTS

| | | | | |
|---|---|---|---|---|
| 5,630,782 | A | * | 5/1997 | Adair ................. A61B 1/12 600/156 |
| 2007/0142711 | A1 | | 6/2007 | Bayer et al. |
| 2008/0195128 | A1 | | 8/2008 | Orbay et al. |
| 2008/0275301 | A1 | * | 11/2008 | Lubowski ............. A61B 1/31 600/130 |
| 2009/0082695 | A1 | | 3/2009 | Whitehead |
| 2009/0198102 | A1 | | 8/2009 | Chen et al. |
| 2009/0231419 | A1 | | 9/2009 | Bayer |
| 2010/0094092 | A1 | | 4/2010 | Barker et al. |
| 2010/0191067 | A1 | | 7/2010 | Chen |
| 2010/0280368 | A1 | * | 11/2010 | Can ................ A61B 17/3417 604/167.03 |
| 2011/0028790 | A1 | | 2/2011 | Farr et al. |
| 2011/0034769 | A1 | | 2/2011 | Adair et al. |
| 2012/0016204 | A1 | | 1/2012 | Bastia |
| 2012/0316391 | A1 | | 12/2012 | Weitzner et al. |
| 2013/0085325 | A1 | | 4/2013 | Fuller et al. |
| 2013/0096378 | A1 | | 4/2013 | Alexander et al. |
| 2013/0096539 | A1 | | 4/2013 | Wood et al. |
| 2013/0204085 | A1 | | 8/2013 | Alexander et al. |
| 2016/0038008 | A1 | | 2/2016 | Molnar |
| 2016/0038012 | A1 | | 2/2016 | McMahon et al. |
| 2016/0302657 | A1 | | 10/2016 | Hussey et al. |
| 2016/0353973 | A1 | | 12/2016 | Mirza et al. |
| 2017/0055813 | A1 | * | 3/2017 | London Brown . A61B 1/00154 |
| 2017/0209027 | A1 | | 7/2017 | Raj et al. |
| 2018/0125350 | A1 | | 5/2018 | Sias |
| 2018/0168433 | A1 | | 6/2018 | Meyer et al. |
| 2018/0326144 | A1 | | 11/2018 | Truckai |
| 2019/0328221 | A1 | | 10/2019 | Wink et al. |
| 2020/0129047 | A1 | * | 4/2020 | Tingvatn ............ A61B 1/00096 |
| 2022/0061650 | A1 | * | 3/2022 | Tingvatn ................ A61B 10/04 |

FOREIGN PATENT DOCUMENTS

| | | | |
|---|---|---|---|
| EP | 1787578 A1 | 5/2007 | |
| EP | 2407090 A1 | 1/2012 | |
| EP | 2599427 A1 | 6/2013 | |
| IT | 1234169 A1 | 5/1992 | |
| WO | 9923812 A2 | 5/1999 | |
| WO | 0160238 A1 | 8/2001 | |
| WO | 2006050574 A1 | 5/2006 | |
| WO | WO-2008135737 A1 * | 11/2008 | ......... A61B 1/00103 |
| WO | 20120151073 A2 | 11/2012 | |
| WO | 2018083330 A1 | 5/2018 | |

OTHER PUBLICATIONS

Advisory Action and AFCP 2.0 Decision for U.S. Appl. No. 16/626,803, mailed Jan. 25, 2022, 5 pages.

Author Unknown, "Proctolux single use Proctoscopes," Griffiths and Nielsen Ltd., 2020, available at https://www.gandn.com/product/proctolux, 3 pages.

Author Unknown, "Sigmolux rigid sigmoidoscope," Griffiths and Nielsen Ltd., 2020, available at https://www.gandn.com/product/sigmolux, 3 pages.

Search Report for United Kingdom Patent Application No. GB1820602.9, mailed May 31, 2019, 5 pages.

Search Report for Norwegian Patent Application No. 20171085, mailed Jan. 26, 2018, 2 pages.

Search Report for Norwegian Patent Application No. 20171736, mailed May 7, 2018, 2 pages.

International Search Report and Written Opinion for International Application No. PCT/NO2018/050170, mailed Oct. 25, 2018, 9 pages.

Invitation to Pay Additional Fees and Partial International Search for International Patent Application No. PCT/EP2019/085643, mailed Mar. 13, 2020, 13 pages.

International Preliminary Report on Patentability for International Patent Application No. PCT/NO2018/050170, mailed Jan. 9, 2020, 6 pages.

International Search Report and Written Opinion for International Application No. PCT/EP2019/085643, mailed Jun. 25, 2020, 19 pages.

Search Report under Section 17(5) for United Kingdom Patent Application No. GB1820602.9 mailed May 31, 2019, 5 pages.

Office Action for U.S. Appl. No. 16/626,803 mailed Feb. 25, 2021, 15 pages.

Extended European Search Report for European Patent Application No. 23191189.2, mailed Nov. 27, 2023, 7 pages.

* cited by examiner

MEDICAL VISUAL EXAMINATION AND SAMPLING DEVICE

CROSS-REFERENCE TO RELATED APPLICATION(S)

This application is a 35 U.S.C. § 371 national phase filing of International Application No. PCT/EP2019/085643 filed on Dec. 17, 2019 and claiming benefit of United Kingdom Patent Application No. 1820602.9 filed on Dec. 18, 2018, wherein the disclosures of the foregoing applications are hereby incorporated by reference herein in their respective entireties.

TECHNICAL FIELD

This invention relates to devices suitable for direct visual examination of a variety of body orifices such as the anus, rectum and vagina.

BACKGROUND

In medical examinations and procedures, a variety of specialized devices such as endoscopes, vaginoscopes, anoscopes and gynaecological specula are used by medical professionals to visually inspect body orifices. As part of such an inspection it may also be necessary to obtain a sample from the body orifice in the region inspected. Conventional devices for performing such tasks often incorporate a lens to aid visual inspection. Owing to necessary restrictions on the size of such device with a view to minimizing the discomfort to the patient, using a lens as a tool for visual inspection can make it impossible to use a sample collection tool whilst viewing the orifice. This makes sample collection difficult and cumbersome, often resulting to an elongated procedure and discomfort to the patient. Many of the conventional devices for performing such procedures are also not optimized so as to provide minimum discomfort to the patient.

Another issue with such conventional devices is contamination. Both the devices and the tools used with the device become contaminated during procedures, and must undergo a lengthy sterilization process after use to avoid cross-contamination between patients.

The Applicant has appreciated it would be advantageous to provide a device for visual inspection of a body orifice that allows for simultaneous visual examination of the orifice and sample collection or inspection using medical equipment.

Furthermore, the Applicant has appreciated it would be further advantageous to provide such a device in a compact form with additional features to minimize discomfort to the patient and to reduce the requirement for sterilization of components.

SUMMARY

When viewed from a first aspect the invention provides a device suitable for direct visual examination and sample collection from the digestive tract and vagina; the device comprising:
a main body;
an observation channel situated inside the main body comprising a first closed end and a second end; and
an obturator for insertion into the main body comprising a longitudinal groove arranged to accommodate the observation channel and a complete convex tip comprising a resiliently deformable portion,
wherein the resiliently deformable portion is adapted to deform to allow the obturator to pass over the observation channel as the obturator is being inserted into the main body and to restore to its original shape once the tip has passed over the observation channel and the obturator is fully inserted into the main body, and wherein restoring the resiliently deformable portion to its original shape results in the tip of the obturator being restored to its original complete convex shape.

Thus. It will be seen by those skilled in the art that in accordance with at least embodiments of this invention, the observation channel allows a medical professional to perform a visual inspection via this channel, whilst the main body may be sealed or instruments may be inserted through the main body. This allows for visual inspection and sample collection to occur simultaneously. The observation channel removes the requirement for a lens on the end of the main body.

The obturator allows for a more comfortable insertion of the device for the patient. By implementing an obturator with a resiliently deformable portion and a longitudinal groove, it is possible for the obturator to be inserted through the main body of the device without damaging or being obstructed by the observation channel. As a result of the resiliently deformable portion restoring to its original shape once the tip has passed over the observation channel (and therefore the tip restoring to its original complete convex shape), a complete convex tip may be presented as the device is inserted into the patient, helping to prevent lubricant used in inserting the device in the orifice collecting on, and so obscuring the view through, the observation channel.

In a set of embodiments, the device is arranged so that upon removal of the obturator after the device has been inserted in the orifice, the resiliently deformable portion is arranged to wipe over and thus clean the closed end of the observation channel. If a complete convex tip was not present, e.g. the tip contained a permanent groove corresponding to the observation channel, then lubricant may collect in this groove when the lubricant is applied to the tip and the device is inserted into the patient. When such an obturator is removed from the main body, the lubricant (and, for example, further materials from the patient) would remain collected in the volume previously occupied by the groove in the tip, obscuring the view through the observation channel. This may make observations through the observation channel difficult.

Once the obturator is removed from the main body of the device, the first closed end of the observation channel is unobstructed. A closure may then be placed on the end of the main body or an instrument inserted through the main body.

In a set of embodiments, the longitudinal groove is identical in shape to the observation channel. The longitudinal groove in preferred embodiments is slightly larger than the observation channel. This allows for the obturator to be inserted through the main body of the device easily without causing any damage to the obturator or observation channel.

To further aid easy insertion and decrease discomfort to the patient, in a set of embodiments the obturator has a rounded tip. It is envisaged that during procedures the tip of the obturator would be covered with a lubricant to further minimize discomfort to the patient. In a set of embodiments, the resiliently deformable portion is spring loaded to ensure the resiliently deformable portion is effectively deployed to restore the original shape of the tip once it has passed over the observation channel, preventing lubricant from entering the main body and obscuring the observation channel.

Whilst the device may be sterilized and re-used for a number of procedures, in a set of embodiments the device is disposable. This increases the efficiency of medical centres performing multiple procedures, as a new device is used for each procedure rather therefore the number of procedures being performed is not limited by the requirement for sterilization of the device in between procedures. This allows centres performing such procedures to increase their effective flow of patients. A disposable device also decreases the risk of cross contamination between patients should issues occur in the sterilization process.

In a set of embodiments, the observation channel contains a visualization device. The visualization devices used may include an optical camera or an infra-red camera. The visualization device in some embodiments is placed towards the closed end of the observation channel to ensure a close view from the end of the device of the orifice. Whilst the visualization device may be connected to further electronics such as a power source and a visual displace system located outside of the device by a cable, it is particularly advantageous for the visualization device to be wireless. Using a visualization device is advantageous over using the naked eye, with or without a lens, to perform a visual inspection as in enables video recording of the procedure, and can enable the medical professional to focus in on areas in the orifice which would not be possible using the naked eye. It also enables the visual inspection to be performed remotely i.e. a doctor may view the image on a screen whilst a nurse performs the procedure. The visualization device may further comprise a light source to enable clearer visualization of the orifice to be obtained. In a set of embodiments, the observation channel is curved, and the visualization device comprises a flexible portion. This allows the visualization device to be inserted into a suitable position in the curved observation channel.

In a set of embodiments, the visualization device is a wireless camera arrangement. In a set of embodiments, the wireless camera arrangement is inserted into the observation channel. The wireless camera arrangement may comprise an optical camera, a wireless transmitter and a battery pack. The wireless camera arrangement may further comprise a light source, and optionally a flexible portion as discussed above. The flexible portion may be situated between the camera portion, and the wireless transmitter and battery pack. In a set of embodiments, a closure is provided on the end the second end of the observation channel which keeps the wireless camera arrangement clean for the duration of the procedure. This preferably provides a water-tight seal on the observation channel. When the procedure has been completed, the closure can be removed from the observation channel and the wireless camera arrangement may be removed by a clean-handed medical professional. By sealing the wireless camera arrangement within the observation channel using the closure, the requirement for thorough sterilization of the wireless camera arrangement after use is removed and this increases the efficiency of the medical procedure.

In a set of embodiments, the closure provides a seal and extends along an end section of the observation channel to form a region of overlap, wherein the wireless visualization device is at least partially disposed within said region of overlap. This provides further measures to ensure that the visualization device is not contaminated during a medical procedure involving the device. The wireless visualization device preferably extends into the region of overlap and when the closure is removed extends, e.g. approximately 2 cm, out of the observation channel, making the visualization device easy to remove without contamination as it can be grasped without touching the end of the observation channel. When in place the closure in such embodiments covers the portion of the wireless visualization device which extends out of the observation channel.

Whilst the Applicant envisages the wireless visualization device can be removed from the device, it is possible to have embodiments in which the wireless visualization device is fixed in position in the observation channel. In such embodiments the closure would not need to be removable. Such arrangement may be utilized in embodiments where the device is intended for re-use. For example, it may in this case be made of a metal.

Preferably, the visualization device is connected (by a wired or wireless connection) to a processor and/or a storage device (e.g. a computer system). The processor may analyse data (e.g. images) obtained by the visualization device. A software program (e.g. running on the processor) may be capable of recognising symptoms of diseases and/or conditions from the data (e.g. images), and may be arranged to provide a suggested diagnosis. The program may include a machine learning algorithm, for example to associate data obtained with diseases and/or conditions.

In a set of embodiments, the device further comprises an inlet for admitting pressurised gas e.g. $CO_2$ or air. The pressurised gas may in use elevate the pressure in the main body of the device. The device may further comprise a pressurising device for providing said elevated pressure in the main body of the device. This allows, for example, for the rectum to be dilated in rectoscopic procedures in order for visual inspection and biopsy of the rectum wall to be performed.

The main body of the device has a first end through which the obturator may be inserted and a second end through which the tip of the obturator emerges upon insertion. Whilst the second end of the main body of the invention described herein may remain open for the duration of the procedure after the obturator is removed, in a set of embodiments an instrument access closure is provided. The instrument access closure provides a seal on an end of the main body to allow an elevated pressure to be maintained. Utilizing an instrument access closure is possible in the invention disclosed, as the observation channel through which a visualization device can be inserted provides a mechanism for visualizing the orifice without needing to see directly through the main body of the device through a lens. In a set of embodiments, the inlet for admitting pressurized gas is provided on the instrument access closure. In a set of embodiments, the pressurising device comprises a bulb (e.g. a hand operated bladder) and a hose.

To maintain the pressure in the device whilst an instrument is inserted for biopsy or other medical purposes, it is desirable for the opening allowing the instrument through the main body of the device to at least partially seal around the instrument. In a set of embodiments, the instrument access closure comprises an aperture. The aperture may be provided by a resilient material with a small perforation. The use of a resilient material allows the instrument access closure to be sealed when no tool is inserted and the aperture to deform around an instrument inserted through the perforation. In some embodiments the instrument access closure is arranged to seal around a circular instrument. In some such embodiments the perforation is circular and suitable for the insertion of tool in order to for example obtain a sample.

In a set of embodiments, the instrument access closure comprises a first part with an aperture and a second part for covering the first part e.g. to protect it from the outside environment and to provide a complete seal when an instrument is not required. The second part may be detached from the first part in order to allow insertion of the tool through the aperture in the first part. The use of a first part and a second part is advantageous as it allows for the pressure in the main body of the device to be maintained for a longer period of time when tools are not being used, so that the rectum can be kept dilated over a longer time period.

The Applicant has appreciated that a device with an instrument access closure is novel and inventive in its own right. Therefore, when viewed from a second aspect the invention discloses a device suitable for direct visual examination of, and sample collection from a body orifice, the device comprising:
 a main body comprising an instrument access closure providing a seal with an aperture suitable for an instrument to be inserted therethrough which forms a seal around the instrument;
 an observation channel situated inside the main body comprising a first closed end and a second end; and
 an inlet for receiving pressurized gas for elevating the pressure in the main body of the device.

Advantageously, to provide additional comfort to the patient, the device in accordance with the second aspect of the invention, further comprises an obturator.

In a set of such embodiments the device further comprises an obturator for insertion into the main body comprising a longitudinal groove arranged to receive the observation channel and a tip comprising a resiliently deformable portion. As previously, the resiliently deformable portion is adapted to deform to allow the obturator to pass over the observation channel as the obturator is being inserted into the main body and to restore to its original shape once the tip has passed over the observation channel and the obturator is fully inserted into the main body.

A person skilled in the art will further appreciate that any of the features described in preceding embodiments may also be features in a set of embodiments relating to the second aspect of the invention.

The Applicant has further appreciated that it would be beneficial to incorporate aspects of the devices described into a gynaecological speculum. Therefore, when viewed from a third aspect the invention discloses a device suitable for direct visual examination and sample collection from a vagina; the device comprising:
 a main body comprising a pair of speculum jaws;
 a handle having a part operable to separate the speculum jaws;
 an observation channel situated inside the main body comprising a first closed end and a second end in the handle;
 a wireless visualization device disposed in the observation channel; and
 a closure on the second end of the observation channel providing a seal wherein the closure extends along an end section of the observation channel to form a region of overlap, wherein the wireless visualization device is at least partially disposed within said region of overlap.

The observation channel contains a wireless visualization device e.g. an optical camera or an infra-red camera. A light source may also be contained within the observation channel or comprise part of the wireless visualization device. Using the closure to seal the visualization device within the observation channel results in the visualization device being contained within a clean zone, therefore the visualization device is kept clean during the procedure. When the procedure has been completed, the closure can then be removed from the observation channel and the wireless visualization device can be removed by a clean-handed medical professional. By sealing the wireless camera arrangement within the observation channel using the second closure, the requirement for thorough sterilization of the wireless camera arrangement after use is removed and this increases the efficiency of the medical procedure.

When viewed from another aspect the invention provides a device suitable for direct visual examination and sample collection from the digestive tract and vagina; the device comprising:
 a main body;
 an observation channel situated inside the main body comprising a first closed end and a second end; and
 an obturator for insertion into the main body comprising a longitudinal groove arranged to accommodate the observation channel and a tip comprising a resiliently deformable portion,
 wherein the resiliently deformable portion is adapted to deform to allow the obturator to pass over the observation channel as the obturator is being inserted into the main body and to restore to its original shape once the tip has passed over the observation channel and the obturator is fully inserted into the main body.

BRIEF DESCRIPTION OF DRAWINGS

Certain embodiments of the present invention will now be described, by way of example only, with reference to the accompanying drawings in which.

DETAILED DESCRIPTION

Figure 1:
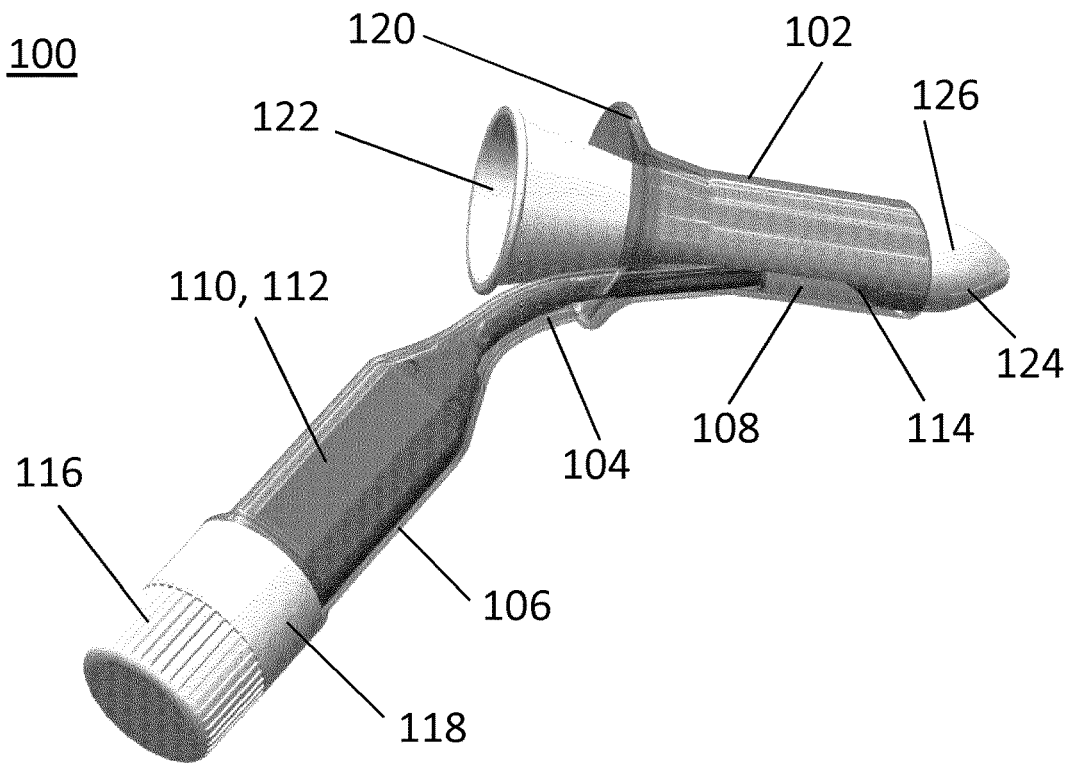
FIG. 1 is a diagram of an endoscope according to an embodiment of the invention.
Figure 2A:
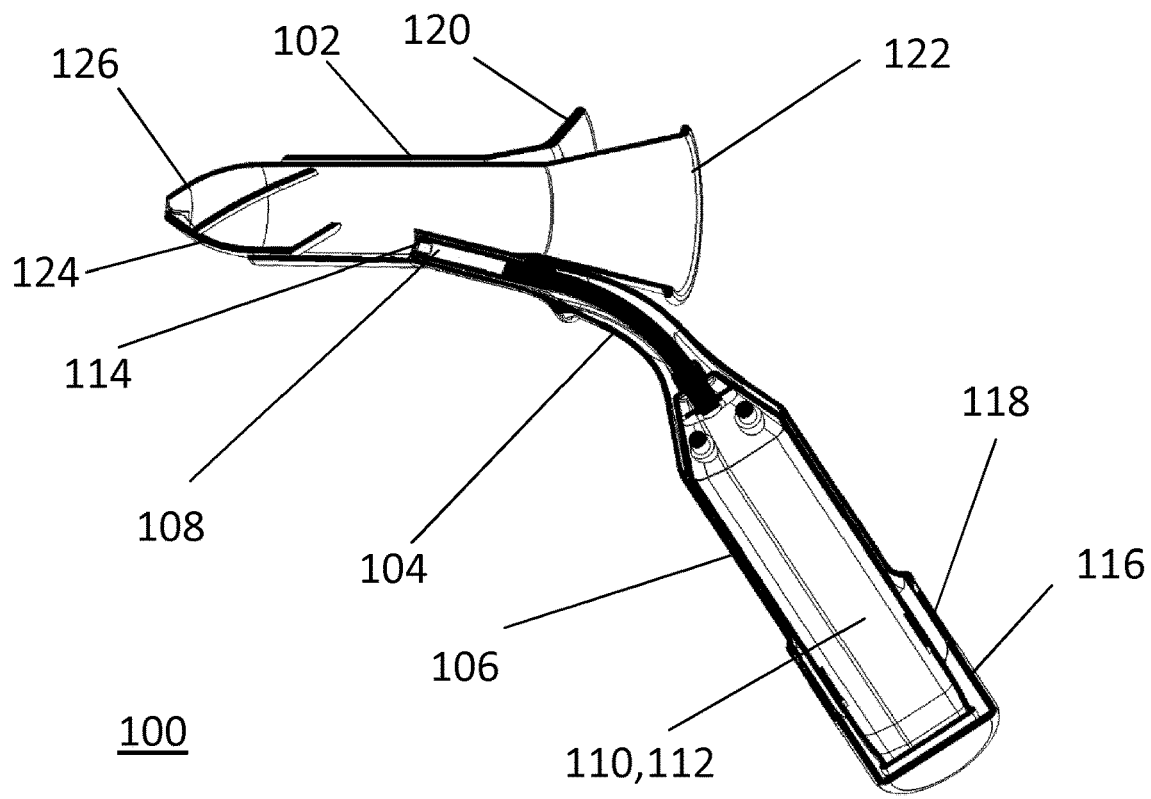
FIG. 2a is a cross-section diagram of the endoscope of FIG. 1.

FIG. 1 illustrates an endoscope 100 in accordance with a first embodiment of the invention and FIG. 2a illustrates a cross-sectional view of such an endoscope. The basic structure of the endoscope 100 includes a rigid tubular main body 102 and a hollow an observation channel 104 which has a closed distal end 114 near the mouth of the main body 102. The observation channel 104 is partially located inside the main body 102 of the endoscope 100 but extends outside of the main body 102. The portion of the observation channel 104 located outside of the main body 102 is bent at an approximately 45° angle to the main body 104. This portion of the observation channel 104 forms the handle 106 of the endoscope 100.

Figure 2B:
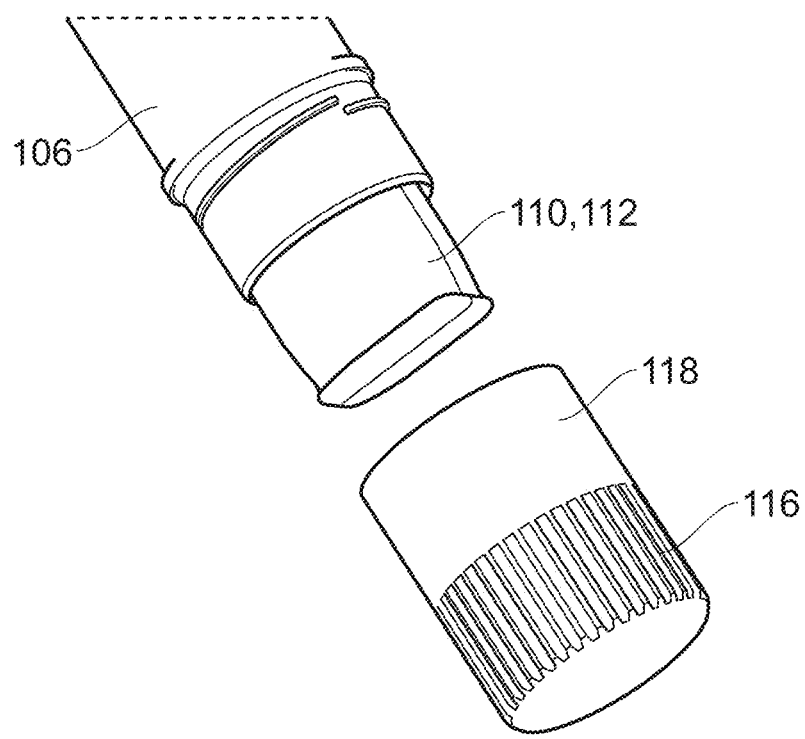
FIG. 2b is a cross-section diagram of the second end of the observation channel and end cap.

A wireless camera arrangement comprising an optical camera 108 with a light source (not shown) connected to a battery pack 110 and a wireless transmitter 112 is inserted into the observation channel 104. The optical camera 108 is positioned at the first transparent, closed end 114 of the observation channel 104. The battery power pack 110 and wireless transmitter 112 are contained with the handle 106 portion of the observation channel 104. A screw cap closure 116 is screwed onto the second end of the observation channel 104 to secure the optical camera 108, battery pack 110 and wireless transmitter 112 inside the observation channel 104. The screw cap closure has a skirt portion 118 that extends over the outside of the end of the observation channel 104 forming a region of overlap. The battery pack 110 and the wireless transmitter 112 are partially located within this region of overlap, and extend partially out of the observation channel when the screw cap closure is removed. The portion of the battery pack 110 and wireless transmitter 112 that extends out of the observation channel 104 is contained within the screw cap closure 116 when the closure is screwed in place as seen in FIG. 2a and FIG. 2b. This configuration prevents the wireless camera arrangement from becoming contaminated during the procedure, removing the need for sterilization of the wireless camera arrangement between uses. Moreover, the configuration aids the removal of the wireless camera arrangement from the device without the wireless camera arrangement being contaminated, as the wireless camera can be grasped without touching any part of the observation channel which has become contaminated.

The main body 102 also comprises a collar 120 to aid positioning of the endoscope. The main body 102 and observation channel 104 are made of a lightweight plastic. At least the first closed end 114 of the observation channel 104 is transparent so that the optical camera can obtain a clear image of the orifice. The main body and observation channel are ideally made for the same transparent lightweight plastic. However, for certain applications it may be beneficial for the endoscope to be re-useable in which case it may be made from a metal, and in such applications the wireless camera may also be fixed in position.

Figure 3:
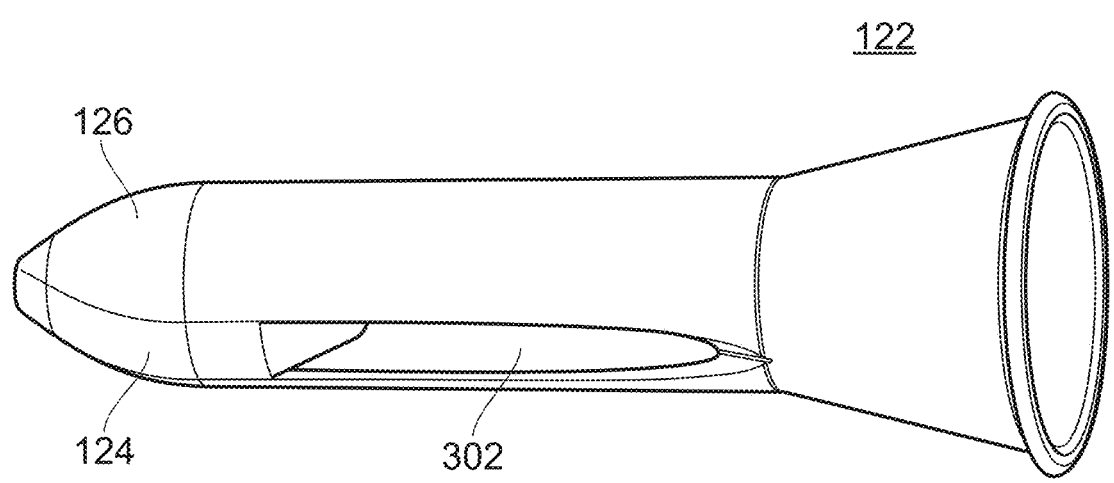
FIG. 3 is a diagram of the obturator with a longitudinal groove and a resiliently deformable portion in accordance with the invention.

In FIG. 1 the obturator 122 is shown inserted into the main body of the endoscope. FIG. 3 shows the obturator 122 in more detail. In this Figure the obturator is in the configuration shown in FIG. 1 where the tip 126 is convex and the resiliently deformable portion 124 is not deformed. A lubricant can then be applied to the tip 126 of the obturator 122 to provide additional comfort to the patient upon insertion of the device. The obturator 122 also has a longitudinal grove 302 which is arranged to accommodate the observation channel 104 when the obturator 122 is inserted into the main body 102 of the endoscope. The endoscope 100, obturator 122 and screw cap closure 116 are made from a lightweight plastic and are disposable.

Figure 4A:
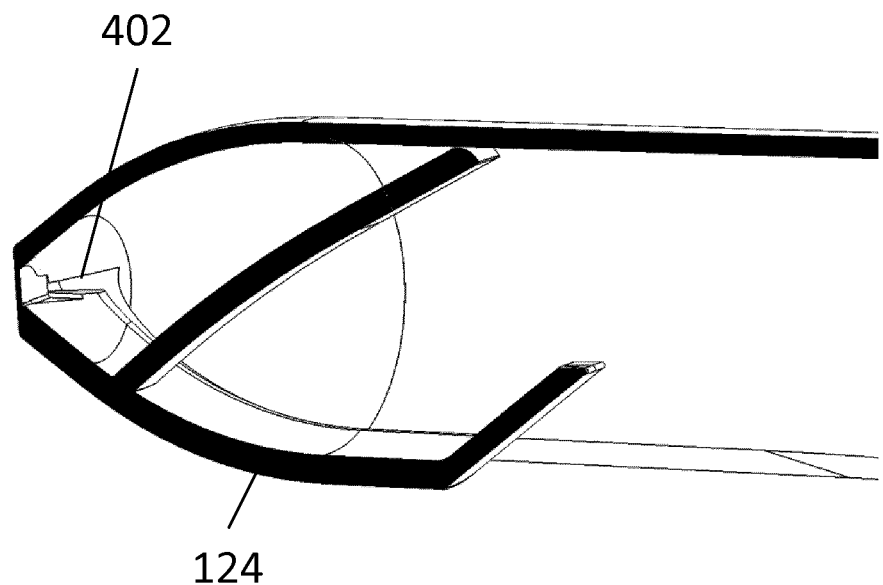
FIG. 4a is a diagram of the resiliently deformable portion of the obturator in its original position forming a convex tip.
Figure 4B:
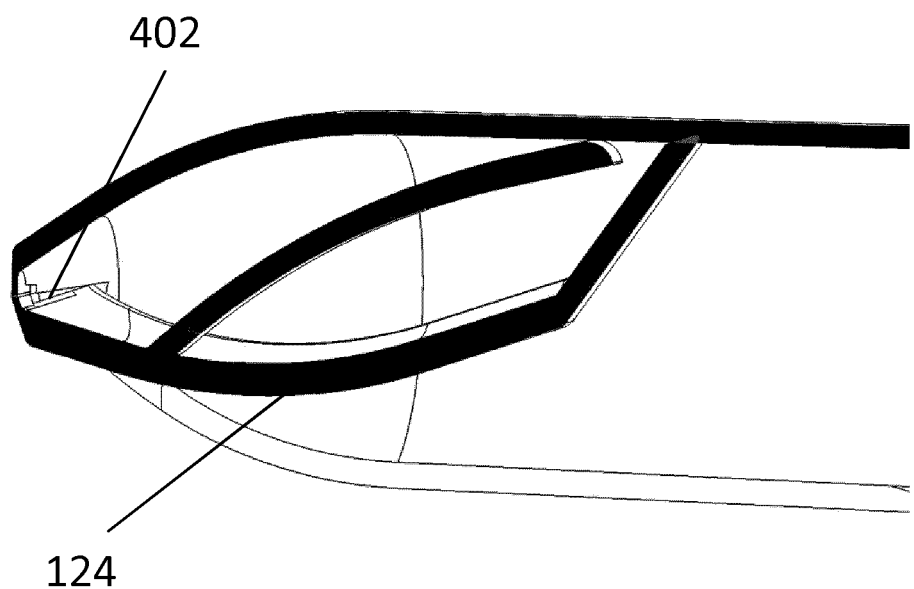
FIG. 4b is a diagram of the resiliently deformable portion of the obturator in a deformed position which allows the obturator to pass over the observation channel.

FIGS. 4a and 4b illustrate a cross-section of the tip 126. In FIG. 4a the resiliently deformable portion 124 is in its original, relaxed position shown in FIGS. 1 and 3. FIG. 4b shows how the resiliently deformable portion 124 is deformed in order to allow the tip 126 to pass over the observation channel 104 as the obturator 122 is inserted into the main body 102 of the endoscope 100. In both Figures a spring mechanism 402 can be seen. The spring mechanism 402 is biased towards the original, relaxed position as seen in FIG. 4a. Therefore, as soon as there is no longer a force acting on the resiliently deformable portion 124 deforming it, i.e. when the obturator 122 is fully inserted into the main body 102 so that the resiliently deformable portion 124 has passed over the observation channel 104, the resiliently deformable portion 124 returns to its original position. This restores the complete shape of the tip 126 so that lubricant gel can be placed on it whilst the end of the observation channel 114 is protected.

Figure 5:
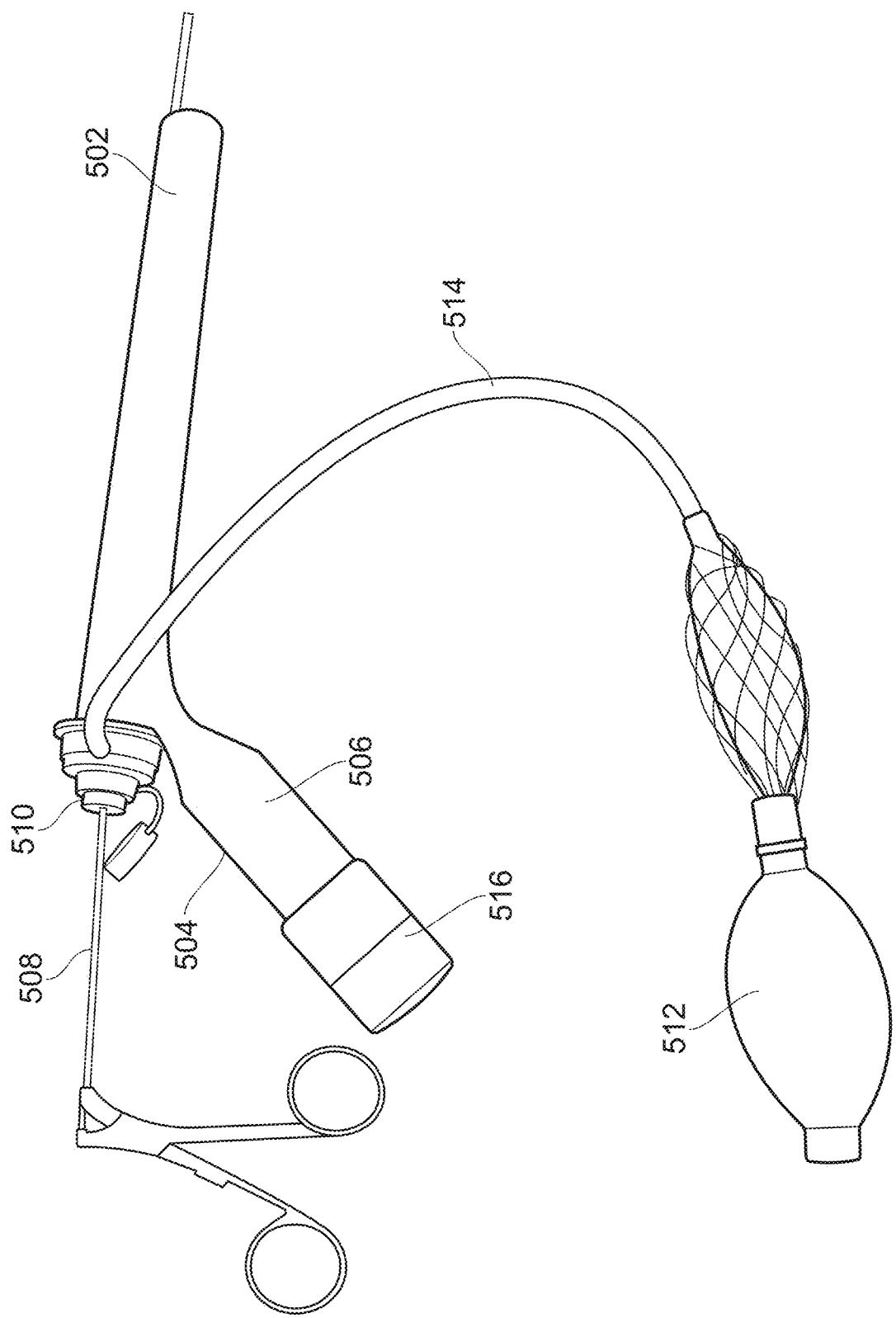
FIG. 5 is a diagram of a rectoscope in accordance with another embodiment of the invention with an instrument inserted through the main body of the device.
Figure 6A:
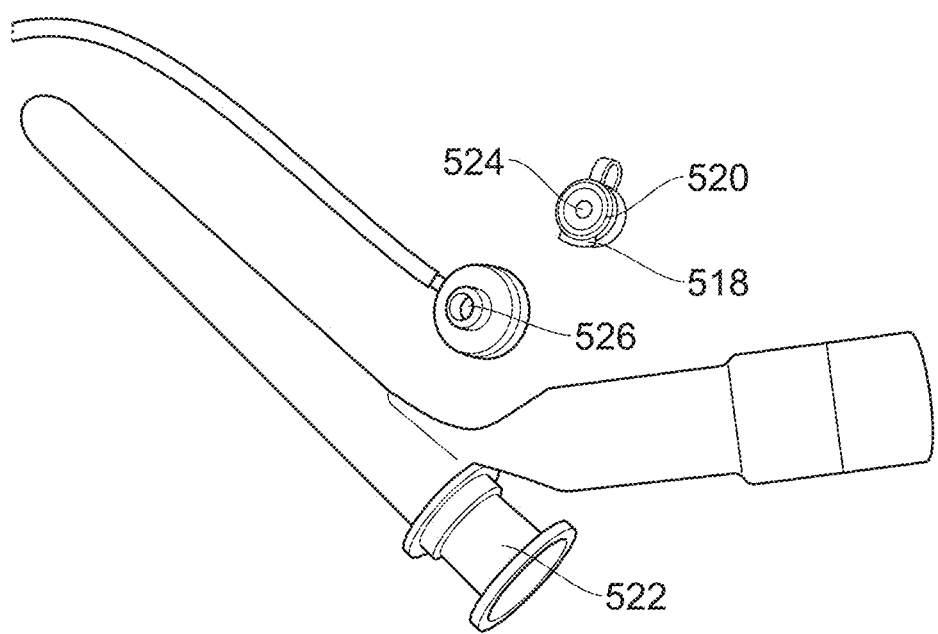
FIG. 6a is a diagram of the instrument access closure with a first part and a second part.

FIGS. 5 and 6 show a different possible embodiment of the invention suitable for use in sample collection from the rectum, known as a rectoscope. The main body 502 of the rectoscope is typically longer in length than the endoscope shown in FIGS. 1 and 2. Similarly to the endoscope seen in FIGS. 1 and 2, the rectoscope comprises a main body 502 and an observation channel 504 wherein part of the observation channel is contained within the main body 502 and part of the observation channel forms a handle 506. A screw cap closure 516 screwed onto the end of the observation channel 504 to secure an optical camera, battery pack and wireless transmitter (not shown in Figure) inside the observation channel 504. An obturator 522 is shown inserted through the main body 502 of the rectoscope in FIG. 6a. The obturator 522 has all the features previously described in the context of FIG. 3, 4a and 4b.

Figure 6B:
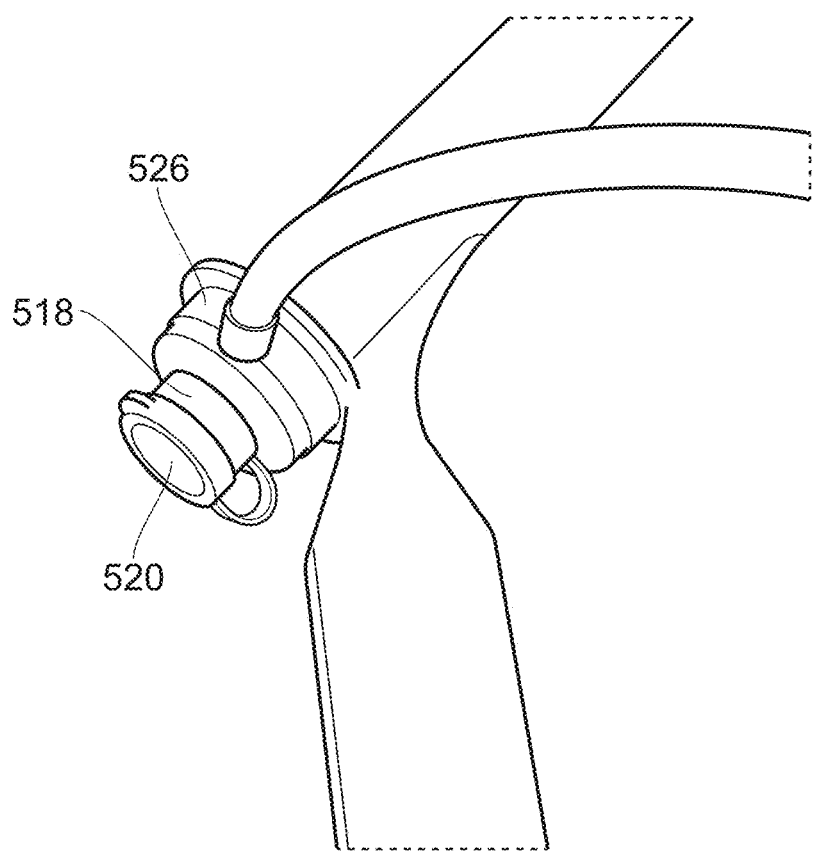
FIG. 6b is an alternative view of the instrument access closure with a first part and a second part when positioned on the main body of the rectoscope.

The rectoscope as shown in FIG. 5, 6a and 6b has a number of additional features. FIG. 5 shows an instrument 508 being inserted through the instrument access closure 510. The instrument access closure 510 is attached to a hand operated bladder/balloon 512 by a hose 514. FIGS. 6a and 6b demonstrate the two parts of the instrument access closure. The first part 518 comprises resilient material such as silicone, in which is defined an aperture 524 through which the instrument 508 can be inserted to perform a biopsy. The first part 518 thus provides at least a partial seal around the instrument 508 to maintain the pressure inside the device. The second part 520 is detachable from the first part 518. When the second part 520 is attached to the first part 518, the second part 520 completely covers the aperture 524 to provide a complete seal when the instrument 508 is not required. The second part 520 is removed in order to allow the instrument 508 to be inserted. A third part 526 of the instrument access closure 510 contains an inlet valve for receiving pressurized gas for elevating the pressure in the main body of the device and this inlet is connected to the hose 514 so that the interior of the device can be inflated by the bladder/balloon 512. It is also possible, although not shown in the figures, for the instrument access closure to be composed of a single part made from a soft material with seals around an inserted instrument.

Figure 7:
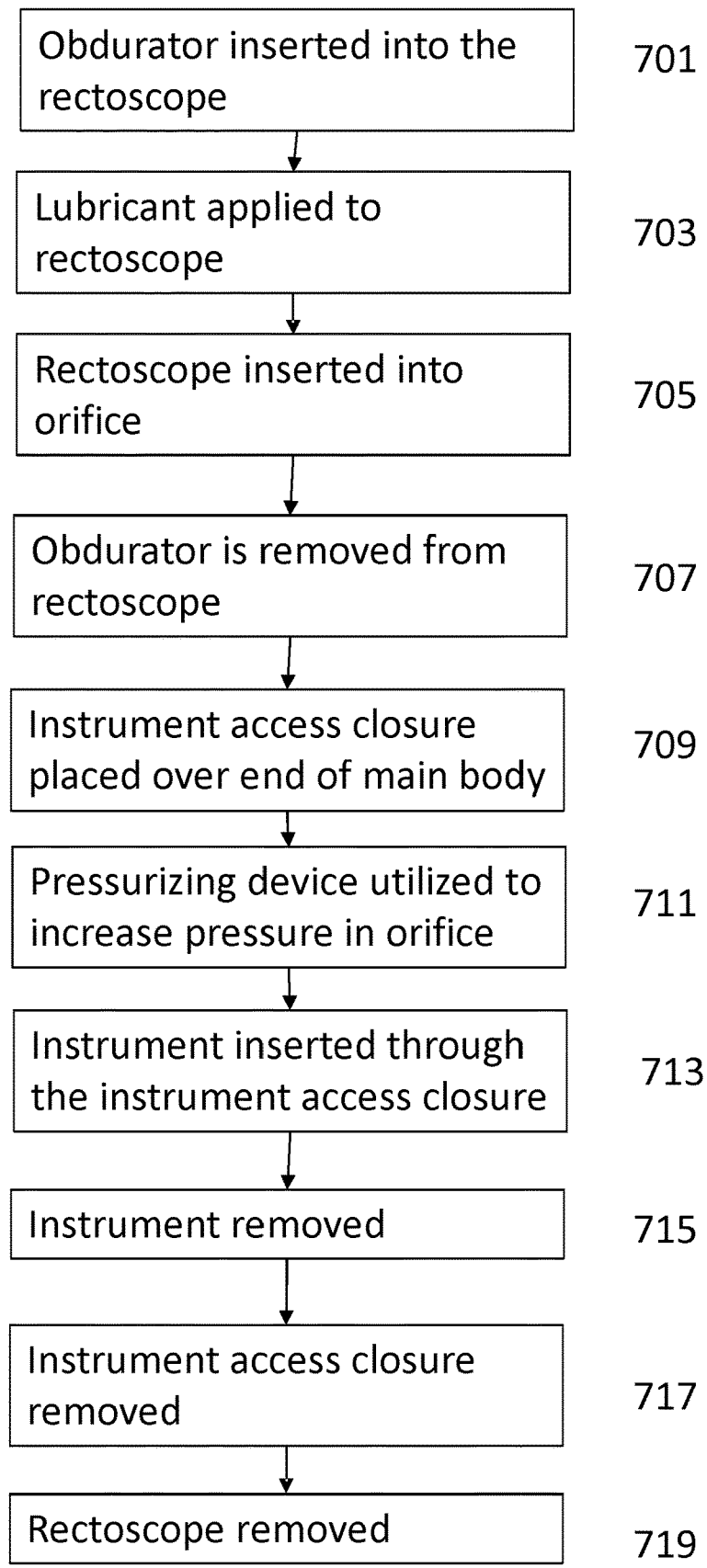
FIG. 7 is a flow chart of the process for obtaining a sample using the rectoscope of FIGS. 5, 6a and 6b.

FIG. 7 is a flow chart of a process of using the rectoscope in order to obtain a sample. In step 701 the obturator is inserted into the rectoscope. In step 703 lubricant is then applied to the rectoscope and obturator, particularly to the tip of the obturator. A medical professional will then insert the rectoscope in the anus and lower parts of the rectum in step 705. Once inserted, the obturator is then removed at step 707. The instrument access closure is then placed over the end of the main body of the rectoscope to form a seal in step 709. In step 711 the pressurizing device is then used to increase the pressure inside the main body of the rectoscope in order to dilate the rectum. A camera in the observation channel may then be used to perform a visual inspection of the rectum. In step 713 an instrument is inserted in order to obtain, for example, a biopsy sample. The instrument is then removed (step 715) and the instrument access closure is removed to reduce the pressure in step 717. The rectoscope is then removed in step 719. The end closure can then be removed and a clean-handed medical professional can remove the camera arrangement without the camera arrangement being contaminated.

Figure 8B:
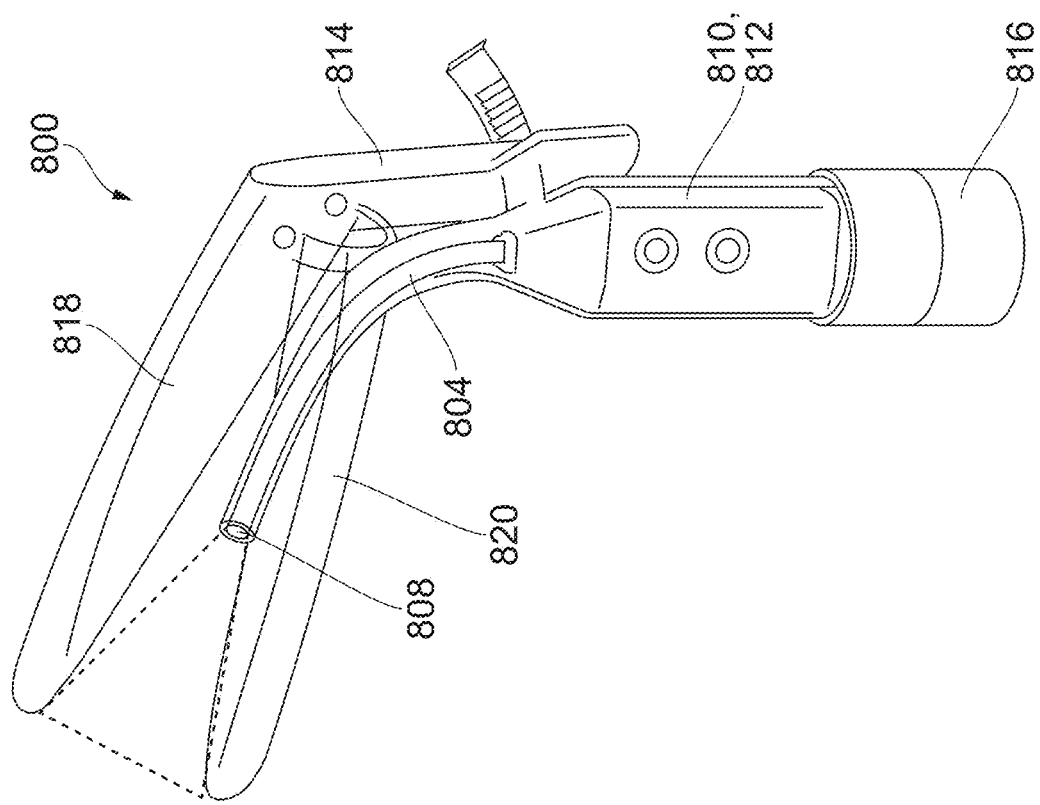
FIG. 8b is a diagram of the gynaecological speculum of FIG. 8a wherein the jaws are open.
Figure 8A:
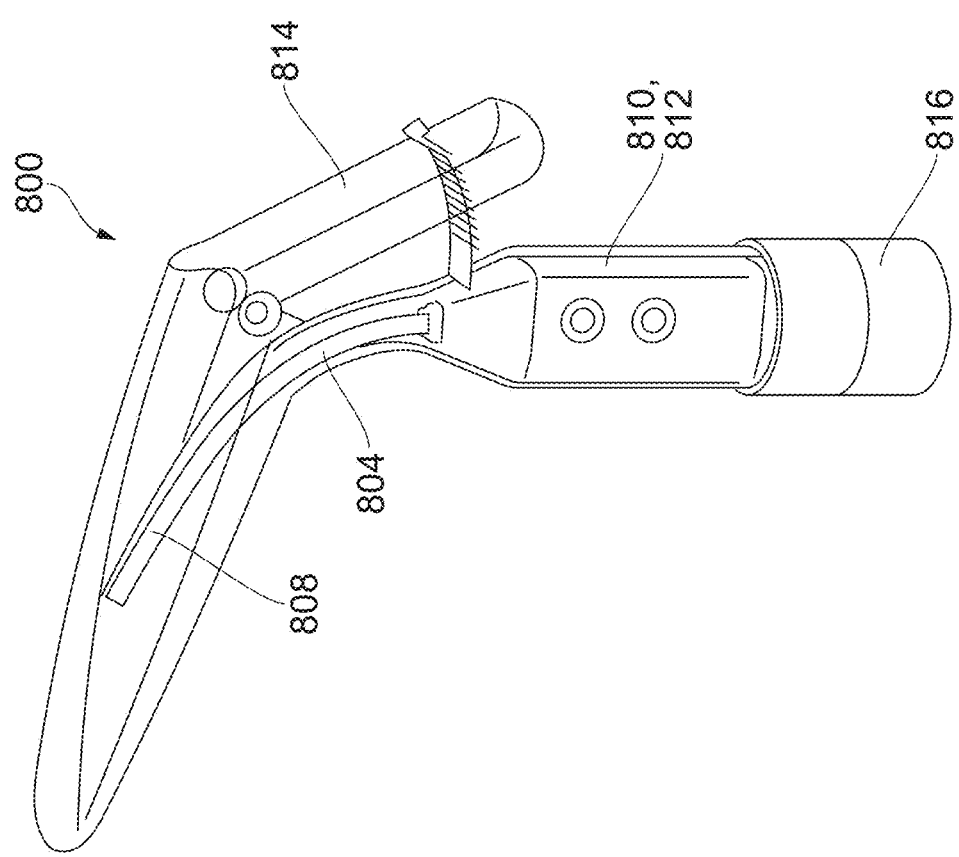
FIG. 8a is a diagram of a gynaecological speculum in accordance with a third aspect of the invention where the jaws are closed.

FIGS. 8a and 8b show a third embodiment of the invention. The Figures show a gynaecological speculum 800 for insertion into a vagina. The gynaecological speculum 800 is formed from a pair of jaws 818, 820 and an observation channel 804. The observation channel 804 has a portion that is disposed between the pair of jaws 818, 820 and a portion situated outside of the jaws 818, 820. Similarly to the endoscope shown in FIGS. 1 and 2, an optical camera 808 is positioned at the first closed end of the observation channel 804. The battery pack 810 and wireless transmitter 812 are contained within the lower portion of the observation channel 804. A screw cap closure 816 is screwed onto the second end of the observation channel 804 to secure the optical camera 808, battery pack 810 and wireless transmitter 812 inside the observation channel 804. This provide a clean sealed region for these instruments, preventing contamination.

FIG. 8a demonstrates the position of the jaws when the speculum is being inserted into a vagina. Once the speculum has been inserted the jaws are opened as seen in FIG. 8b by operating the jaw handle 814. This opens the vagina enabling a clear visualization using the optical camera 808.

Thus, it will be appreciated by those skilled in the art that the specific embodiments of the inventive concepts described herein provide devices suitable for direct visual examination of a variety of body orifices such as the rectum, anus or vagina. This may provide significant benefits over known devices. It will further be appreciated that many variations of the specific arrangements described here are possible within the scope of the invention.

The invention claimed is:

1. A device suitable for direct visual examination and sample collection from the digestive tract or vagina; the device comprising:
   a tubular main body comprising an inner wall defining a volume;
   an observation channel comprising a first closed end and a second end; and
   an obturator for insertion into the volume defined by the inner wall of the tubular main body, wherein the obturator comprises:
   a longitudinal groove arranged to accommodate the observation channel; and a tip,
   wherein the tip has a complete convex shape that is devoid of a groove arranged to accommodate the observation channel, and the tip has a resiliently deformable portion,
   wherein at least a portion of the observation channel is situated inside the tubular main body, and protrudes from the inner wall of the tubular main body;
   wherein, when the obturator is inserted into the volume defined by the inner wall of the tubular main body, the observation channel is situated outside of the obturator; and
   wherein the resiliently deformable portion of the tip is configured to deform to allow the obturator to pass over the observation channel as the obturator is being inserted into the volume defined by the inner wall of the tubular main body and configured to restore to its original shape once the tip has passed over the observation channel and the obturator is fully inserted into the volume defined by the inner wall of the tubular main body, and wherein restoring the resiliently deformable portion to its original shape results in the tip of the obturator being restored to its original complete convex shape that is devoid of a groove arranged to accommodate the observation channel.

2. A device as claimed in claim 1 wherein upon removal of the obturator after the device has been inserted in the digestive tract or vagina, the resiliently deformable portion is arranged to wipe over and thus clean the first closed end of the observation channel.

3. The device as claimed in claim 1 wherein the tip of the obturator is rounded.

4. The device as claimed in claim 1 wherein the resiliently deformable portion is spring loaded.

5. The device as claimed in claim 1 wherein the device is disposable.

6. The device as claimed in claim 1 wherein the observation channel contains a visualization device.

7. The device as claimed in claim 6 wherein the visualization device comprises an optical camera.

8. The device as claimed in claim 1 wherein the observation channel is curved.

9. The device as claimed in claim 6 wherein the visualization device comprises a flexible portion.

10. The device as claimed in claim 1 wherein a closure is provided on the second end of the observation channel.

11. The device as claimed in claim 10 wherein the closure provides a seal and extends along an end section of the observation channel to form a region of overlap, wherein the observation channel contains a wireless visualization device that is at least partially disposed within said region of overlap.

12. The device as claimed in claim 11 wherein the wireless visualization device is arranged such that when the closure is removed, the wireless visualization device extends out of the observation channel.

13. The device as claimed in claim 1 further comprising an inlet for admitting pressurized gas.

14. The device as claimed in claim 1 further comprising an instrument access closure.

15. The device as claimed in claim 14 wherein the instrument access closure provides a seal on an end of the tubular main body to allow an elevated pressure to be maintained.

16. The device as claimed in claim 14 further comprising an inlet for admitting pressurized gas that is provided on the instrument access closure.

17. The device as claimed in claim 14 wherein the instrument access closure comprises an aperture.

18. The device as claimed in claim 17 wherein the aperture is provided by a perforation in a resilient material.

19. The device as claimed in claim 18 wherein the perforation is circular.

20. The device as claimed in claim 14 wherein the instrument access closure comprises a first part defining an aperture and a second part configured to cover the first part, wherein the second part is detachable from the first part.

* * * * *